(12) United States Patent
Ohashi et al.

(10) Patent No.: US 7,379,586 B2
(45) Date of Patent: May 27, 2008

(54) COLOR VISION CHARACTERISTIC DETECTION APPARATUS

(75) Inventors: Shinichi Ohashi, Kanagawa (JP); Shinsuke Sugi, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 569 days.

(21) Appl. No.: 11/053,850

(22) Filed: Feb. 10, 2005

(65) Prior Publication Data
US 2005/0213039 A1 Sep. 29, 2005

(30) Foreign Application Priority Data
Mar. 10, 2004 (JP) ............ P2004-067280

(51) Int. Cl.
*G06K 9/00* (2006.01)
(52) U.S. Cl. ............ 382/162; 382/167; 382/274; 382/305; 351/242; 351/200; 345/594; 345/589
(58) Field of Classification Search ............ 382/162, 382/164, 165, 166, 167, 274, 305; 351/242, 351/200, 222, 239; 345/594, 589, 581
See application file for complete search history.

(56) References Cited
U.S. PATENT DOCUMENTS
5,801,809 A * 9/1998 Husain ............ 351/239

7,264,356 B2 * 9/2007 Jones et al. ............ 351/242
2001/0053246 A1 * 12/2001 Tachibana et al. ............ 382/162
2004/0223641 A1 * 11/2004 Koyama et al. ............ 382/162
2005/0105051 A1 * 5/2005 Jones et al. ............ 351/242

OTHER PUBLICATIONS

"Diversity of color vision and color vision barrier-free presentation, part 1", Okabe and Ito, Cell Technology, Shujunsha, vol. 21, No. 7, Jul. 2002, pp. 733-745.
"Diversity of color vision and color vision barrier-free presentation, part 2", Okabe and Ito, Cell Technology, Shujunsha, vol. 21, No. 8, Aug. 2002, pp. 909-930.

* cited by examiner

*Primary Examiner*—Matthew C. Bella
*Assistant Examiner*—Ali Bayat
(74) *Attorney, Agent, or Firm*—Morgan, Lewis & Bockius LLP

(57) ABSTRACT

A color vision characteristic detection apparatus has a storage section, a generation section, and a presenting section. The storage section stores a basic color chart containing portions colored in colors different from each other. The generation section performs a predetermined conversion processing with respect to the basic color chart to generate an adjusted color chart for one color vision characteristic type so that it is difficult for a person who has a visual characteristic of the one color vision characteristic type to distinguish the adjusted color chart from the basic color chart. The presenting section presents the basic color chart and the adjusted color chart to a user.

3 Claims, 4 Drawing Sheets

_US 7,379,586 B2_

COLOR VISION CHARACTERISTIC DETECTION APPARATUS

BACKGROUND OF THE INVENTION

1. Field of the Invention

The invention relates to an apparatus for detecting the color vision characteristic of a user to adjust an image presented by an information processing apparatus and in particular to improvement of the convenience of the apparatus.

2. Description of the Related Art

In recent years, a color display (display formed of a liquid crystal panel, an organic EL panel, etc.,) has been installed in a personal computer, a mobile telephone, a PDA (Personal Digital Assistant), further in a vending machine of tickets, etc., for example, and has been useful for presenting various pieces of information.

However, the display may not necessarily be easy to understand for those who have congenital color vision impairment or acquired color vision impairment. Hitherto, various methods for presenting an image in a mode, which facilitates color vision perception, have been proposed ("Diversity of color vision and color vision barrier-free presentation, part 1", Okabe and Ito, Cell Technology, Shujunsha, Vol. 21, No. 7, July 2002, pp. 733-745 and "Diversity of color vision and color vision barrier-free presentation, part 2", Okabe and Ito, Cell Technology, Shujunsha, Vol. 21, No. 8, August 2002, pp. 909-930).

However, there are large variations among individuals in the color vision impairment state in such a manner that the color vision impairment type differs; in fact, the mode facilitating color vision perception as in the related art described above varies from one person to another. However, hitherto, as for the variations among individuals, for example, the types of congenital color vision impairment (there are three types of P, D, and T) have been only able to be set. A user often does not know his or her type. As with the acquired color vision impairment, if the degree of difference between individuals is large, it is not easy to make setting for each individual within the given types.

SUMMARY OF THE INVENTION

The invention provides a color vision characteristic detection apparatus for making it possible to easily set color vision perception support considering variations among individuals.

To address the problems in the related arts described above, according to one embodiment of the invention, a color vision characteristic detection apparatus has a storage section, a presenting section, and a determination section. The storage section stores at least one piece of first image data and at least one piece of second image data. The first image data has pattern element sets containing (a) a first pattern element set colored in a color belonging to a first set of colors confusing to a person who has a visual characteristic of a first color vision characteristic type, and (b) a second pattern element set colored in a color belonging to a second set of colors confusing to a person who has a visual characteristic of a second color vision characteristic type. The first pattern element set defines a first symbol character shape. The second pattern element set defines a second symbol character shape, which is different from the first symbol character shape. The second image data that has a third pattern element set colored in a color belonging to a third set of colors confusing to a person who has a visual characteristic of a third color vision characteristic type. The presenting section presents the first image data to a user. The determination section accepts a user's entry of information concerning a symbol read from the first image data presented and determines based on the entered information whether or not the second image data is to be presented to the user. Accordingly, determination for each type is facilitated.

The storage section may store plural pieces of the first image data. The presenting section may present plural pieces of the first image data to the user. The determination section may accept user's entries of information concerning symbols read from the plural pieces of first image data presented and determine based on the entered information whether or not the second image data is to be presented to the user. Thus, if it is allowed to use plural pieces of first image data, it is becomes possible to present plural pieces of first image data, which are made different in condition involved in variations among individuals for each type. As a result, color vision perception support considering variations among individuals can be set easily.

Also, to solve the problems in the related arts described above, according to one embodiment of the invention, a color vision characteristic detection apparatus has a storage section, a generation section, and a presenting section. The storage section stores a basic color chart containing portions colored in colors different from each other. The generation section performs a predetermined conversion processing with respect to the basic color chart to generate an adjusted color chart for one color vision characteristic type so that it is difficult for a person who has a visual characteristic of the one color vision characteristic type to distinguish the adjusted color chart from the basic color chart. The presenting section presents the basic color chart and the adjusted color chart to a user.

According to one embodiment of the invention, a color vision characteristic detection method causes a computer to execute the following processing. The computer has a storage section that stores at least one piece of first image data and at least one piece of second image data. The first image data has pattern element sets containing (a) a first pattern element set colored in a color belonging to a first set of colors confusing to a person who has a visual characteristic of a first color vision characteristic type, and (b) a second pattern element set colored in a color belonging to a second set of colors confusing to a person who has a visual characteristic of a second color vision characteristic type. The first pattern element set defines a first symbol character shape. The second pattern element set defines a second symbol character shape, which is different from the first symbol character shape. The second image data that has a third pattern element set colored in a color belonging to a third set of colors confusing to a person who has a visual characteristic of a third color vision characteristic type. The processing includes presenting the first image data to a user; accepting a user's entry of information concerning a symbol read from the first image data presented; and determining based on the entered information whether or not the second image data is to be presented to the user.

According to one embodiment of the invention, a color vision characteristic detection method causes a computer to execute the following processing. The processing includes storing a basic color chart containing portions colored in colors different from each other; performing a predetermined conversion processing with respect to the basic color chart to generate an adjusted color chart for one color vision characteristic type so that it is difficult for a person who has a visual characteristic of the one color vision characteristic type to distinguish the adjusted color chart from the basic color chart; and presenting the basic color chart and the adjusted color chart to a user.

BRIEF DESCRIPTION OF THE DRAWINGS

An embodiment of the invention will be described in detail based on the following figures, wherein.

DETAILED DESCRIPTION OF THE INVENTION

Figure 1:
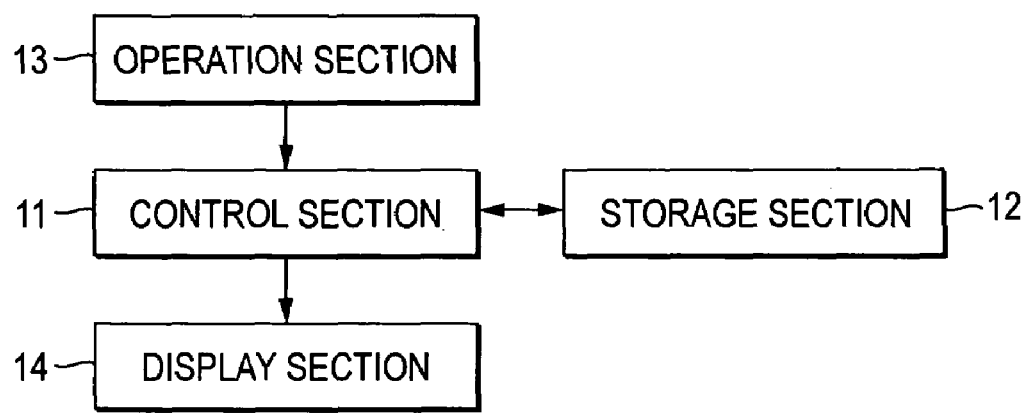
FIG. 1 is a block diagram to show a configuration example of a color vision characteristic detection apparatus according to an embodiment of the invention.

Referring now to the accompanying drawings, an embodiment of the invention will be described. A color vision characteristic detection apparatus according to the embodiment has a control section 11, a storage section 12, an operation section 13, and a display section 14, as shown in FIG. 1. The control section 11 operates in accordance with a program stored in the storage section 12, presents image data to a user, accepts a response from the user, and determines the color vision characteristic of the user (color vision characteristic determination processing). The storage section 12 is a memory or a disk unit for retaining the program executed by the control section 11 and the image data presented by the control section 11. The specific description of the program and the specific form of the image data will be discussed later in detail.

The operation section 13 includes input units of a keyboard, a pointing device (pen, mouse, etc.,), and the like, accepts user's operation, and outputs content of the user's operation to the control section 11. The display section 14 is a color display panel such as a CRT or a liquid crystal display. The display section 14 displays image data in accordance with an instruction input from the control section 11.

The specific form of the image data presented by the control section 11 will be discussed. One piece of the image data presented by the color vision characteristic detection apparatus according to the embodiment contains a first pattern element set and a second pattern element set. The first pattern element set is colored in colors belonging to a first set of colors which are confusing to a person who has the visual characteristic of a first color vision characteristic type. The second pattern element set is colored in colors belonging to a second set of colors which are confusing to a person who has the visual characteristic of a second color vision characteristic type. In the first pattern element set and the second pattern element set, symbol character shapes are formed using different colors, which belong to the first and second pattern element sets, respectively.

Figure 2:
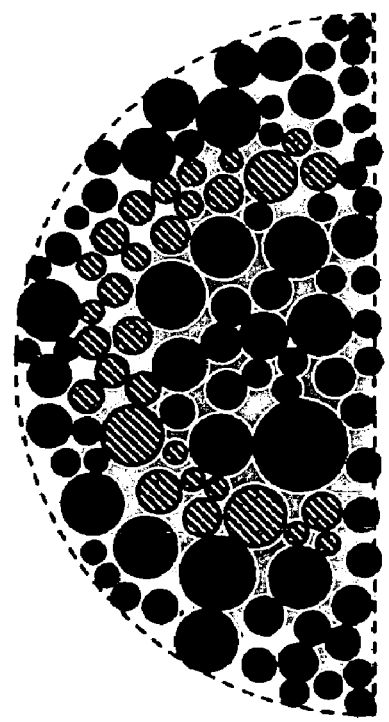
FIG. 2 is a schematic representation to show an example of image elements.

Specifically, as for one specific color vision characteristic, schematically in FIG. 2, the colors perceived as roughly the same color by a person who does not have the specific color vision characteristic are represented by the same hatching. Colors perceived as different colors by a person who does not have the specific color vision characteristic, but perceived as roughly the same color by a person who has the specific color vision characteristic are represented by the different hatchings. Pattern elements (in FIG. 2, circles) colored using the colors perceived as roughly the same color by a person who does not have the specific color vision characteristic are arranged for representing a symbol letter shape "C". That is, the pattern shown in FIG. 2 is designed so that the letter shape "C" is not visually recognized by the person who has the specific color vision characteristic, but is visually recognized by any other person. Such a pattern is widely known with the name of pseudoisochromatic plates, etc., and therefore will not be discussed here in detail.

In this embodiment, plural patterns are prepared and presented in combination to make it hard for persons who have different color vision characteristics to recognize the involved letter shapes. Specifically, there are three basic types of color vision impairment (P, D, and T). Then, for example, a first pattern (first pattern element set) visually recognized as letter "C" by a person who is not of the P type and a second pattern (second pattern element set) visually recognized as letter "D" by a person who is not of the D type are combined to generate one image (first image data shown in FIG. 3).

Therefore, a person of the P type would be able to read the generated image as "D" (only the character shape in the second pattern element set is visually recognized); likewise, a person of the D type would be able to read the image as "C"; and a person who is of neither P nor D type (with no color vision impairment or T type) would be able to read the image as "CD".

Figure 3:
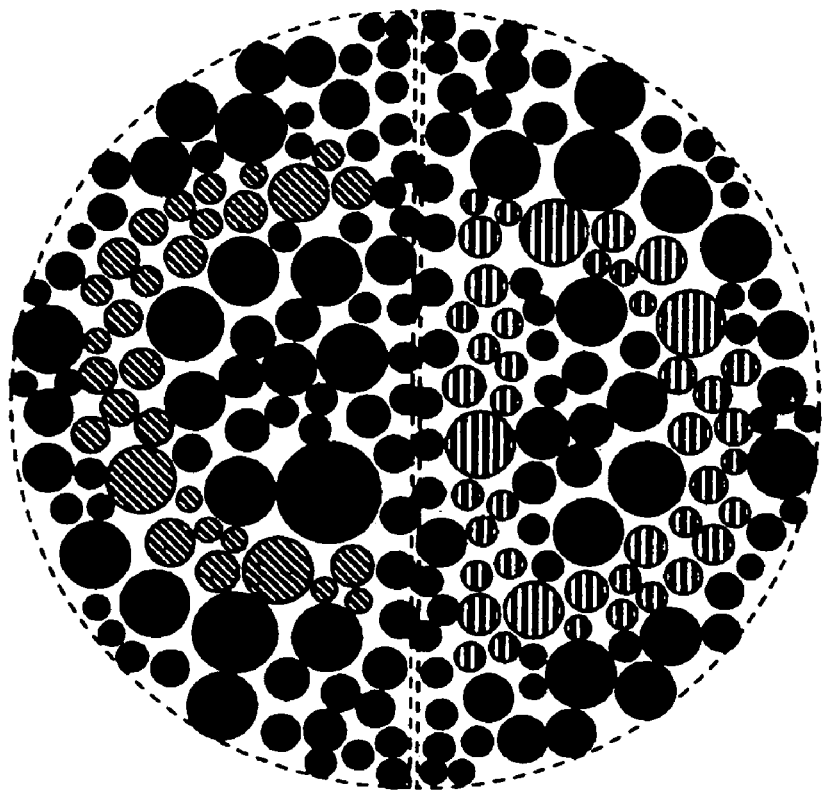
FIG. 3 is a schematic representation to show an example of a first presented image.

In FIGS. 2 and 3, the dashed line surrounding each pattern element set is shown, but is not necessarily needed and is shown for representing the outline of each pattern element set. Plural first image element sets and plural second image element sets (image element sets involving different character shapes) may be stored in the storage section 12. When first image data is to be generated, the control section 11 may randomly select and read one of the first image element sets and one of the second image element sets and may combine the read image element sets to generate one piece of image data (first image data). Here, the two image element sets are combined, but a larger number of image element sets may be combined to generate first image data.

To combine the image element sets as in FIG. 3, each of the plural first image element sets has a semicircular shape of a left half of a circle and each of the plural second image element sets has a semicircular shape of a right half of a circle.

Figure 4:
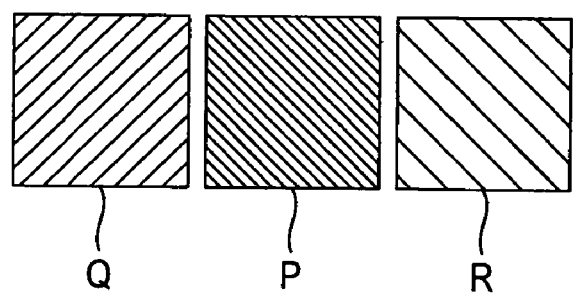
FIG. 4 is a schematic representation to show an example of a second presented image.

Another piece of image data presented by the control section 11 includes a third pattern element set colored in colors belonging to a third set of colors confusing to a person who has the visual characteristic of a third color vision characteristic type different from the first and second color vision characteristic types, as shown in FIG. 4.

Specifically, the third pattern element set is generated based on the principle similar to D15 test. The D15 test is a test for making a test subject arrange 15 color patches in the color similarity order and determining the color vision characteristic of the test subject based on the arrangement result. Here, a first color (Q) and a second color (R) are defined. The first color (Q) is confused with (perceived as similar color to) a predetermined center color (P) by a person of the third color vision characteristic type, but not confused with the center color by a person of any other color vision characteristic type. The second color (R) is not confused with the predetermined center color by a person of the third color vision characteristic type, but confused with the center color by a person of any other color vision characteristic type. Pattern elements (for example, square patterns) colored in these colors are arranged as shown in FIG. 4 to generate an image containing the third pattern element set (second image data) The arrangement order and the color combination are not limited to them.

The control section 11 of the embodiment performs the following processing using the image data. That is, when a user enters a command to start setting the color vision characteristic, the control section 11 starts processing shown in FIG. 5. The control section 11 reads one of first pattern element sets and one of second pattern element sets from the storage section 12, combines the first and second pattern element sets to generate one piece of image data (first image data) (S1), and displays the generated image on the display section 14 together with a message such as "Enter all visible characters." (a first message for requesting the user to specify the visually recognizable characters) (S2). Then, the control section 11 waits for the user to enter characters and checks which of (a) only the character involved in the first pattern element set, (b) only the character involved in the second pattern element set, or (c) the characters involved in both the first and second pattern element sets (S3) the user enters.

If the user enters (a) only the character involved in the first pattern element set, the control section 11 determines that the visual characteristic of the user is the first color vision characteristic type (S4) and terminates the processing. If the user enters (b) only the character involved in the second pattern element set, the control section 11 determines that the visual characteristic of the user is the second color vision characteristic type (S5) and terminates the processing.

Further, if the user enters (c) the characters involved in both the first and second pattern element sets, the control section 11 generates image data containing a third pattern element set (second image data) (S6). In the generated image data, pattern elements have a square shape and are arranged in a row. The pattern element colored in the center color is placed at the center and is sandwiched between squares colored in first and second colors (as shown in FIG. 4).

The control section 11 displays the image generated at step S6 on the display section 14 together with a message such as "Which color is close to the color shown at the center?" (a second message for requesting the user to enter a color close to the center color) (S7). Then, the control section 11 waits for the user to enter characters and determines the color vision characteristic type of the user based on the user's entry (S8) Specifically, if the entry is information specifying the first color, the control section 11 determines that the visual characteristic of the user is the third color vision characteristic type (S9) and terminates the processing. Further, if the entry is information specifying the second color, the control section 11 determines that the visual characteristic of the user does not fall under any of the first to third color vision characteristic types (S10) and terminates the processing.

That is, if the control section 11 determines that the visual characteristic of the user is the first or second color vision characteristic type, the control section 11 does not perform processing to determine whether or not the visual characteristic is the third color vision characteristic type.

Specifically, if the first pattern element set is set so that a person who has the color vision impairment of the P type (an example of the first color vision characteristic type) cannot visually recognize the character involved in the pattern element set; if the second pattern element set is set so that a person who has the color vision impairment of the D type (an example of the second color vision characteristic type) cannot visually recognize the character involved in the pattern element set; and if the third pattern element set is set so that a person who has the color vision impairment of the T type (an example of the third color vision characteristic type) can see that the center color and the first color are similar (that is, confuse the two colors), the control section 11 determines the color vision characteristic type of the user according to the processing described above.

The determination result is used when the control section 11 adjusts color for image data subjected to display processing. For example, if the control section 11 concludes that a person has the color vision impairment of the P type, which is the first color vision characteristic type, contours, hatching, and the like are generated using the colors confused by the person who has the color vision impairment of the P type.

Here, the control section 11 carries out a test similar to the pseudoisochromatic plate test and the D15 test using the display section 14 and determines the color vision characteristic type of the user, but the test method is not limited thereto. For example, plural color patches may be provided, the user may be instructed to classify the patches into two types according to the category of color difference, and the color vision characteristic type of the user may be determined based on the result of the classification into the category. For example, if red, green, yellow, and yellow green color patches are presented, a user with no color vision impairment would classify the color patches into the category of red and the category involving green, yellow, and yellow green. However, a user who has the color vision characteristic of the P type or the D type would visually recognize that red and green are roughly the same color or that yellow and yellow green are roughly the same color, and therefore would classify the color patches into a category made up of red and green and a category made up of yellow and yellow green. Thus, the color vision characteristic type can be determined based on the classification (category) difference.

In the description made so far, tests similar to the pseudoisochromatic plate test and the D15 test are conducted each once and then, the color vision characteristic type of the user is determined. However, for example, there are slight color vision impairment and profound color vision impairment. Also, there is color vision characteristic caused by an acquired factor such as cataract (different from P, D, T type). Therefore, test processing using each image may be executed more than once.

For example, a cataractous patient becomes difficult to make color vision perception for blue as the crystalline lens of the patient is colored. Then, for example, when the control section 11 determines that the visual characteristic of the user does not fall under any of the first to third color vision characteristic types (S9 in FIG. 5), in order to further examine color vision perception for blue, the control section 11 may present plural images different in blue component, may receive the user's entry of information specifying the images recognized as the same by the user, and may determine the visual characteristic of the user for blue.

Figure 5:
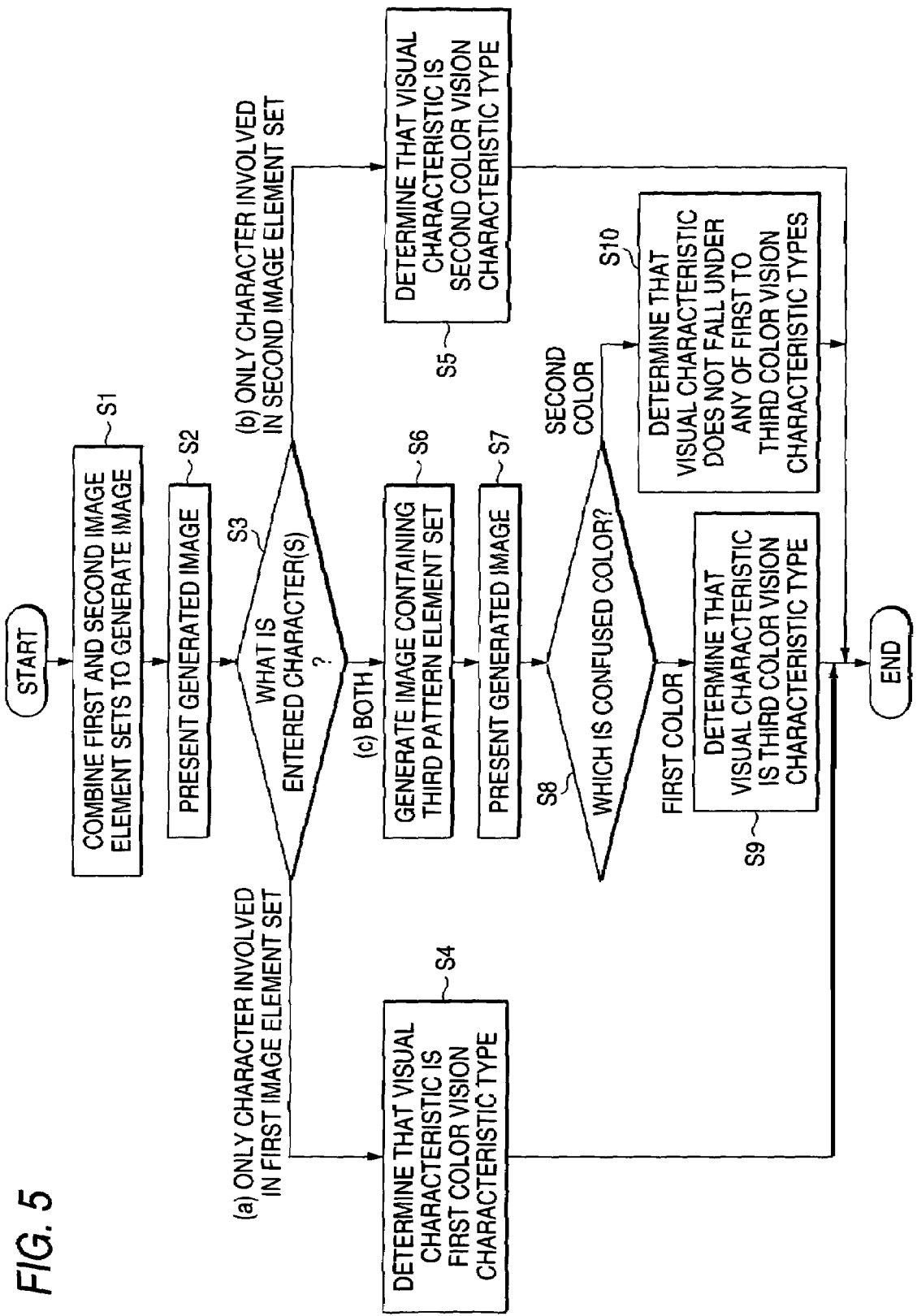
FIG. 5 is a flowchart to show an example of processing executed by a control section.

Steps S1 to S3 in FIG. 5 may be repeated for generating and presenting two or more images each containing the first and second image element sets and determining the color vision characteristic type of the user based on the result.

Also, steps S6 to S8 in FIG. 5 may be repeated for generating and presenting two or more images each containing the third image element set and determining the color vision characteristic type of the user based on the result.

Further, if the control section 11 concludes that the visual characteristic of a user is the first color vision characteristic type at step S4 in FIG. 5, the control section 11 may further present an image containing the first image element set for again checking the visual characteristic of the user.

Further, the pseudoisochromatic plates used here (FIGS. 3 and 4) are set so that it is difficult for a person of the first or second color vision characteristic type to recognize the character shape; in contrast, the pseudoisochromatic plates may be set so that a person of the first or second color vision characteristic type can recognize the character shape and that it is difficult for any other person to recognize the character shape. In this case, if a person can recognize the character shape, the control section 11 concludes that the person is of the corresponding color vision characteristic type.

Further, in addition to the pseudoisochromatic plates and D15 test (similar to panel D15), the control section 11 may determine the color vision characteristic type of a user as follows: A basic color chart containing portions colored in different colors (or a basic color chart with color gradations) is stored in the storage section 12 in advance. The control section 11 performs predetermined conversion processing so as to make it impossible to discriminate the converted one from the basic color chart according to the color vision characteristic involved in at least one color vision characteristic type to generate an adjusted color chart for each color vision characteristic type. Then, the control section 11 presents the basic color chart and the generated adjusted color charts on the display section 14 for requesting a user to specify which adjusted color chart is the same as the basic color chart.

Figure 6A:
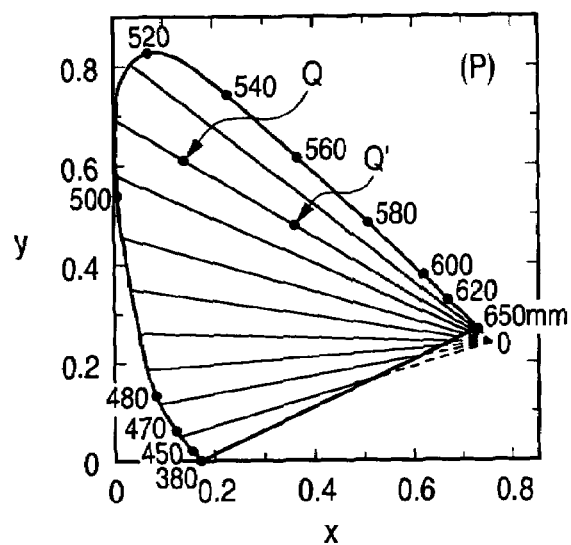
FIGS. 6A to 6C are schematic representations to show the state of a confused color line for each of color vision characteristic types.
Figure 6B:
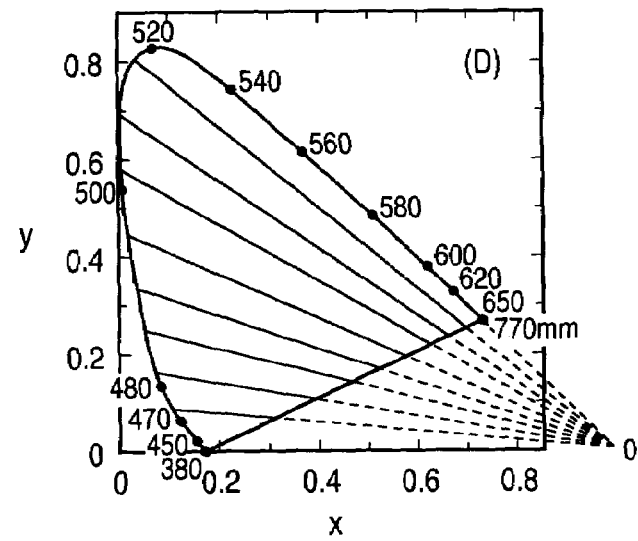
Figure 6C:
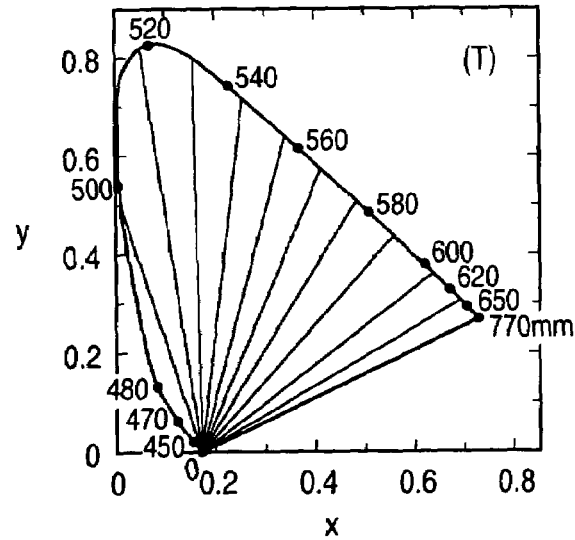

Specifically, a spectrum map with colors arranged in the wavelength order is used as a basic color chart and colors on the basic color chart are moved along the confused color line (FIG. 6) defined for each type of P, D, T (for example, assuming that a color at a point Q in FIG. 6A exists on the basic color chart, the color is moved to another color at a point Q') so that the colors on the spectrum map cannot be discriminated from the basic color chart in the corresponding color vision characteristic for each type of P, D, T.

The move can be made by using line segment expression for representing each confused color line, $y=\alpha x+\beta$, and acquiring another xy coordinate value on the same line segment as the xy coordinate value of Q.

A color chart provided by moving the colors (adjusted color chart) can be discriminated from the basic color chart by the user of a different color vision characteristic type from the P type, for example, but cannot be discriminated from the basic color chart by the user of the color vision characteristic type of the P type.

The control section 11 generates adjusted color charts corresponding to the types, displays the basic color chart and the generated adjusted color charts on the display section 14 together with a message of "Which chart is the same as basic color chart? If you cannot find the same, enter X" or the like, accepts the user's entry of specifying the adjusted color chart recognized as the same as the basic color chart, and determines that the visual characteristic of the user is the type corresponding to the specified adjusted color chart.

The foregoing description of the embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

The entire disclosure of Japanese Patent Application No. 2004-067280 filed on Mar. 10, 2004 including specification, claims, drawings and abstract is incorporated herein by reference in its entirety.

What is claimed is:

1. A color vision characteristic detection apparatus comprising:
    a storage section that stores at least one piece of first image data that comprises pattern element sets containing:
        a first pattern element set colored in a color belonging to a first set of colors confusing to a person who has a visual characteristic of a first color vision characteristic type;
        a second pattern element set colored in a color belonging to a second set of colors confusing to a person who has a visual characteristic of a second color vision characteristic type, wherein the first pattern element set defines a first symbol character shape and the second pattern element set defines a second symbol character shape, which is different from the first symbol character shape;
    at least one piece of second image data that comprises a third pattern element set colored in a color belonging to a third set of colors confusing to a person who has a visual characteristic of a third color vision characteristic type;
    a presenting section that presents the first image data to a user; and
    a determination section that accepts a user's entry of information concerning a symbol read from the first image data presented and determines based on the entered information whether or not the second image data is to be presented to the user.

2. The color vision characteristic detection apparatus according to claim 1, wherein:
    the storage section stores a plurality of pieces of the first image data;
    the presenting section presents a plurality of pieces of the first image data to the user; and
    the determination section accepts user's entries of information concerning symbols read from the plurality of pieces of first image data presented and determines based on the entered information whether or not the second image data is to be presented to the user.

3. A color vision characteristic detection method for causing a computer that comprises a storage section that stores at least one piece of first image data that comprises pattern element sets containing:
    a first pattern element set colored in a color belonging to a first set of colors confusing to a person who has a visual characteristic of a first color vision characteristic type;
    a second pattern element set colored in a color belonging to a second set of colors confusing to a person who has a visual characteristic of a second color vision characteristic type, wherein the first pattern element set defines a first symbol character shape and the second pattern element set defines a second symbol character shape, which is different from the first symbol character shape; and at least one piece of second image data that comprises a third pattern element set colored in a color belonging to a third set of colors confusing to a person who has a visual characteristic of a third color vision characteristic type, to execute processing comprising:

presenting the first image data to a user;

accepting a user's entry of information concerning a symbol read from the first image data presented; and determining based on the entered information whether or not the second image data is to be presented to the user.

\* \* \* \* \*